United States Patent
Harding

(10) Patent No.: US 8,366,684 B2
(45) Date of Patent: Feb. 5, 2013

(54) INTRAVENOUS CATHETER BLOOD CONTROL DEVICE

(75) Inventor: Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1170 days.

(21) Appl. No.: 12/119,351

(22) Filed: May 12, 2008

(65) Prior Publication Data

US 2009/0281481 A1    Nov. 12, 2009

(51) Int. Cl.
*A61M 5/00* (2006.01)
(52) U.S. Cl. .......... 604/246; 604/537; 604/167.01; 604/167.03; 604/167.04
(58) Field of Classification Search ......... 604/167.01–167.05, 246, 249, 604/256, 537; 251/149.1, 149.6, 149.7
See application file for complete search history.

(56) References Cited

U.S. PATENT DOCUMENTS

| | | |
|---|---|---|
| 3,811,440 A | 5/1974 | Moorehead et al. |
| 3,856,010 A | 12/1974 | Moorehead et al. |
| 3,895,632 A | 7/1975 | Plowiecki |
| 3,977,400 A | 8/1976 | Moorehead |
| 4,387,879 A | 6/1983 | Tauschinski |
| 4,449,693 A | 5/1984 | Gereg |
| 4,657,772 A | 4/1987 | Kocak |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 5,041,097 A | 8/1991 | Johnson |
| 5,053,014 A | 10/1991 | Van Heugten |
| 5,061,253 A | 10/1991 | Yoshida |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,098,394 A | 3/1992 | Luther |
| 5,108,374 A | 4/1992 | Lemieux |
| 5,108,380 A | 4/1992 | Herlitze et al. |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,295,969 A | 3/1994 | Fischell et al. |
| 5,330,435 A | 7/1994 | Vaillancourt |

(Continued)

FOREIGN PATENT DOCUMENTS

| | | |
|---|---|---|
| CA | 2133053 A1 | 3/1995 |
| WO | WO 99/34849 | 7/1999 |

(Continued)

*Primary Examiner* — Kevin C Sirmons
*Assistant Examiner* — Laura Schell
(74) *Attorney, Agent, or Firm* — Jeanne Lukasavage; Craig Metcalf; Kirton McConkie

(57) ABSTRACT

An apparatus to control blood flow through an intravenous catheter in accordance with the present invention may include a substantially resilient helical outer shell and an inner valve portion formed therein. The inner valve portion may be configured to open upon compressing the substantially resilient helical outer shell. In some embodiments, the inner valve portion may include mating portions that substantially align to provide fluid leakage therebetween. Compressing the substantially resilient helical outer shell by, for example, inserting a Luer device into a catheter adapter containing the substantially resilient outer shell, may cause the mating portions to misalign, thereby creating a fluid path.

20 Claims, 6 Drawing Sheets

U.S. PATENT DOCUMENTS

| | | | |
|---|---|---|---|
| 5,350,363 A | 9/1994 | Goode et al. | |
| 5,352,205 A | 10/1994 | Dales et al. | |
| 5,380,305 A | 1/1995 | Ghouri | |
| 5,405,323 A | 4/1995 | Rogers et al. | |
| 5,429,616 A | 7/1995 | Schaffer | |
| 5,456,675 A | 10/1995 | Wolbring et al. | |
| 5,487,728 A | 1/1996 | Vaillancourt | |
| 5,514,114 A | 5/1996 | Soto-Tolosa et al. | |
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,657,963 A * | 8/1997 | Hinchliffe et al. | 251/149.1 |
| 5,697,915 A | 12/1997 | Lynn | |
| 5,738,144 A | 4/1998 | Rogers | |
| 5,749,857 A | 5/1998 | Cuppy | |
| 5,749,861 A | 5/1998 | Guala et al. | |
| 5,782,816 A | 7/1998 | Werschmidt et al. | |
| 5,806,831 A | 9/1998 | Paradis | |
| 5,817,069 A | 10/1998 | Arnett | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 * | 8/2001 | Vaillancourt | 604/86 |
| 6,485,473 B1 | 11/2002 | Lynn | |
| 6,575,960 B2 | 6/2003 | Becker et al. | |
| 6,595,981 B2 | 7/2003 | Huet | |
| 6,699,221 B2 | 3/2004 | Vaillancourt | |
| 6,740,063 B2 | 5/2004 | Lynn | |
| 6,883,778 B1 | 4/2005 | Newton et al. | |
| 6,994,315 B2 * | 2/2006 | Ryan et al. | 251/149.6 |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| 7,736,339 B2 | 6/2010 | Woehr et al. | |
| 7,914,494 B2 | 3/2011 | Hiejima | |
| 2004/0044313 A1 | 3/2004 | Nakajima | |
| 2004/0167474 A1 | 8/2004 | Meng et al. | |
| 2006/0155245 A1 | 7/2006 | Woehr | |
| 2007/0083162 A1 | 4/2007 | O'Reagan et al. | |
| 2008/0039796 A1 | 2/2008 | Nakajima | |
| 2008/0108944 A1 | 5/2008 | Woehr et al. | |
| 2010/0204675 A1 | 8/2010 | Woehr et al. | |

FOREIGN PATENT DOCUMENTS

| | | |
|---|---|---|
| WO | 01/49363 A1 | 7/2001 |
| WO | 2007/050788 A2 | 5/2007 |

* cited by examiner

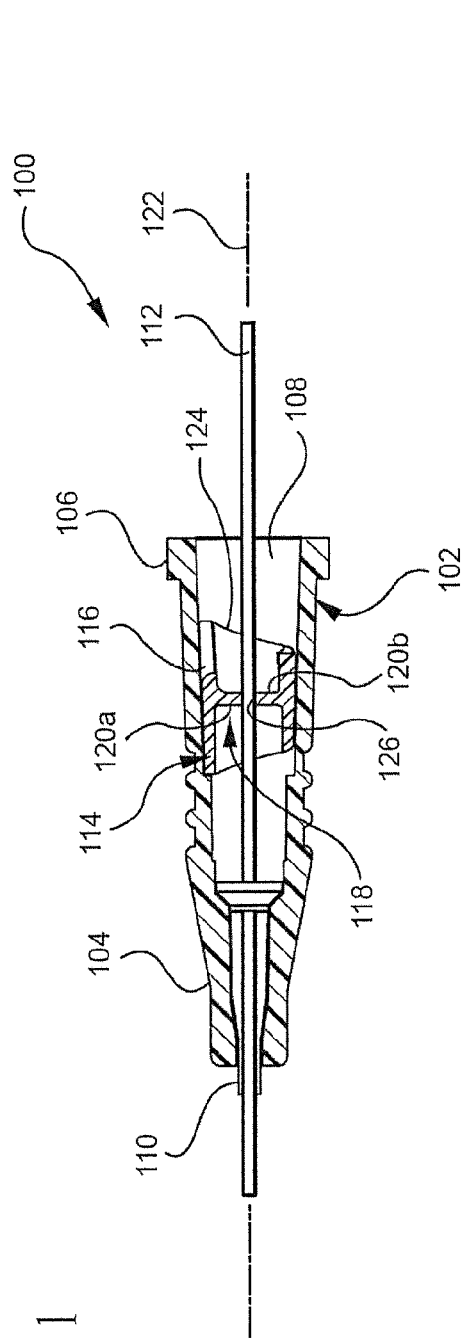
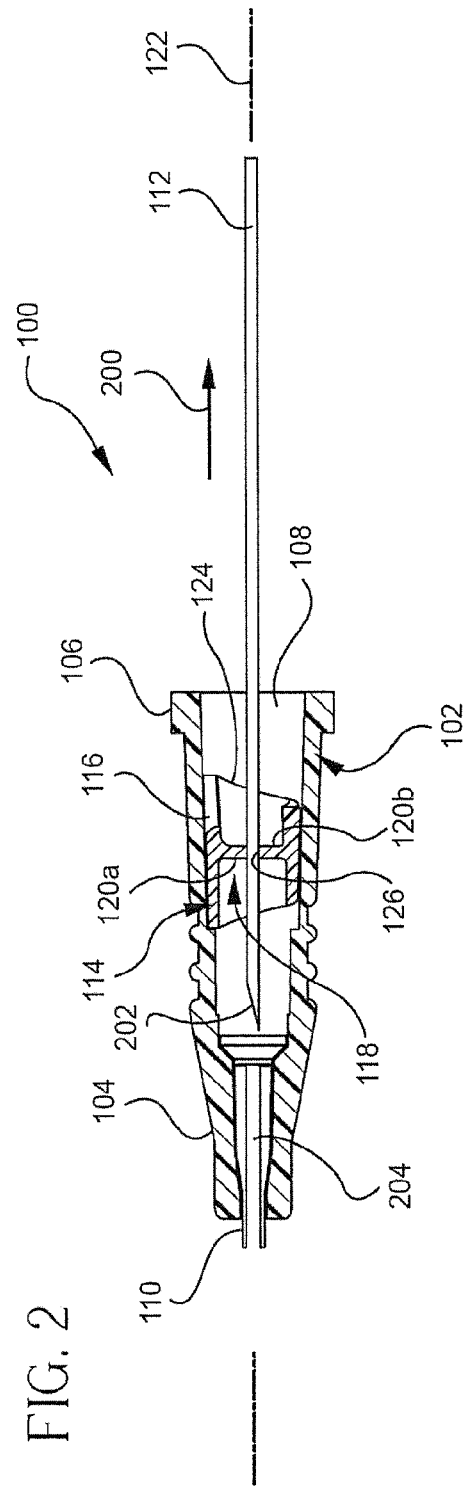
FIG. 1
FIG. 2

INTRAVENOUS CATHETER BLOOD CONTROL DEVICE

BACKGROUND

This disclosure relates generally to medical assemblies for fluid administration, and more particularly to closed-system intravenous catheter assemblies that reduce a potential for blood exposure during insertion and use.

The insertion of an intravenous catheter into a patient's bloodstream is one of the most commonly performed procedures in health care environments today. Such catheters are widely used to infuse fluids, such as saline solution, various medicaments, and/or total parenteral nutrition into a patient. They may also be used to withdraw blood from a patient, and/or monitor various parameters of the patient's vascular system.

Despite their prevalence and usefulness in health care environments, procedures used for intravenous catheter insertion present significant risks to the health care workers that perform them. Particularly, health care workers are at an increased risk for contracting viral hepatitis, Human Immunodeficiency Virus ("HIV"), the virus that causes Autoimmune Deficiency Virus ("AIDS"), and other blood-borne infectious diseases. This risk is increased as intravenous catheter insertion requires disassembly of the introducer needle from the catheter adapter once the catheter is properly positioned within a patient's bloodstream. This process requires a high level of dexterity and physical manipulation, with an accompanying increased risk of exposure to blood and blood pathogens.

To introduce an IV catheter into a patient, an over-the-needle catheter may be mounted over a hollow-bore introducer needle having a sharp distal tip. The inner surface of the catheter may tightly engage the outer surface of the needle to prevent catheter peelback and facilitate insertion of the catheter into a blood vessel. The tip of the introducer needle may extend beyond the distal tip of the catheter to enable insertion of the catheter at a shallow angle through the patient's skin and into a blood vessel.

To verify proper placement of the needle and catheter in the blood vessel, the clinician may confirm the presence of "flashback" blood in a flashback chamber associated with the catheter and needle assembly. Once proper placement is initially confirmed, the clinician may then remove the needle from the catheter and apply pressure to the blood vessel to occlude the vessel, thereby controlling further blood flow into the catheter assembly. This technique, however, is imprecise and may result in blood from the blood vessel exiting the catheter tube through the catheter adapter, thereby compromising sterility of the fluid path and potentially exposing the health care worker to blood and blood pathogens.

The requirement to apply digital pressure to the blood vessel after insertion of the catheter also leaves the health care worker with only one hand available to manipulate the catheter insertion assembly as needed to remove the needle and connect the catheter adapter to the administration set. This requirement thus further increases the potential for human error resulting in blood exposure and injuries related thereto.

Finally, typical catheter insertion practice requires the catheter to be further advanced into the blood vessel upon withdrawing the needle therefrom. While blood control valves exist to reduce an incidence of blood flow beyond the open end of the catheter adapter, such valves tend to impair a health care worker's continued ability to verify proper positioning of the catheter, since blood flashback may only be observed upon initial placement. Accordingly, known blood control valves tend to increase a potential for catheter failure and procedure duplication.

From the foregoing discussion, it should be apparent that a need exists for an intravenous catheter blood control device capable of controlling blood flow to facilitate visibility of blood flashback throughout a catheter insertion procedure, while minimizing a risk of blood exposure from blood spills through the catheter adapter. Beneficially, such an intravenous catheter blood control device would enable simple and inexpensive manufacture, simple and effective operation, and high adaptability for use in connection with presently available standard insertion assemblies. Such an intravenous catheter blood control device is disclosed and claimed herein.

BRIEF SUMMARY

The present invention has been developed in response to the present state of the art, and in particular, in response to the problems and needs in the art that have not yet been met by currently available intravenous catheter blood control devices. Accordingly, the present invention has been developed to provide an intravenous catheter blood control device that overcomes many or all of the above-discussed shortcomings in the art.

An apparatus to control blood flow through an intravenous catheter in accordance with embodiments of the present invention may include a substantially resilient helical outer shell and an inner valve portion formed therein. The substantially resilient helical outer shell may include an elastomeric material, such as silicone rubber. The inner valve portion may be configured to open upon compressing the substantially resilient helical outer shell.

In one embodiment, the inner valve portion includes mating portions that substantially align to provide controlled fluid leakage therebetween. Compressing the substantially resilient helical outer shell may cause the mating portions to misalign to create a fluid path. In some embodiments, the mating portions are configured to receive a needle therebetween.

In certain embodiments, the substantially resilient helical outer shell is configured to be retained within a catheter adapter. The outer shell may be oriented within the catheter adapter such that a Luer device inserted into the catheter adapter compresses the outer shell, and, in some cases, translates at least a portion of the outer shell towards a catheter coupled to an end of the catheter adapter.

A method to control blood flow through an intravenous catheter in accordance with embodiments of the present invention is also presented. The method may include providing a substantially resilient helical outer shell and forming within the outer shell an inner valve portion. The outer shell may include an elastomeric material and may be positioned within a catheter adapter. In certain embodiments, the outer shell may be oriented within the catheter adapter such that a Luer device inserted therein compresses the substantially resilient helical outer shell to open the inner valve portion.

In some embodiments, the inner valve portion may include mating portions molded within the substantially resilient helical outer shell. The mating portions may substantially align to provide controlled fluid leakage therebetween. Compressing the outer shell may cause the mating portions to misalign to create a fluid path. In certain embodiments, the mating portions may be made of an elastomeric material and may selectively deform to receive a needle therebetween.

The method may further include inserting the Luer device into the catheter adapter to compress the substantially resilient helical outer shell. In one embodiment, inserting the Luer device into the catheter adapter translates at least a portion of the outer shell towards a catheter coupled to an end of the catheter adapter.

An intravenous catheter assembly to control fluid flow through an intravenous catheter in accordance with the present invention may include piercing means for piercing a blood vessel to acquire intravenous access, and intravenous catheter means for providing fluid communication between the blood vessel and fluid administration means for administering a fluid to a patient. The intravenous catheter assembly may further include valve means for controlling fluid flow through the intravenous catheter means. The valve means may include substantially resilient helical outer shell means for positioning within the intravenous catheter means to mediate fluid flow, and inner valve means for creating a fluid path upon compressing the substantially resilient helical outer shell means.

The substantially resilient helical outer shell means may be oriented within the intravenous catheter means such that a Luer device inserted into the intravenous catheter means compresses the substantially resilient helical outer shell means to open the inner valve means. In some embodiments, the inner valve means may include mating means for providing controlled fluid leakage therebetween.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1 is a cross-sectional view of a blood control device integrated into an intravenous catheter assembly in accordance with certain embodiments of the present invention;

FIG. 2 is a cross-sectional view of the blood control device and intravenous catheter assembly of FIG. 1 showing withdrawal of the needle following catheter insertion;

DETAILED DESCRIPTION

Figure 3A:
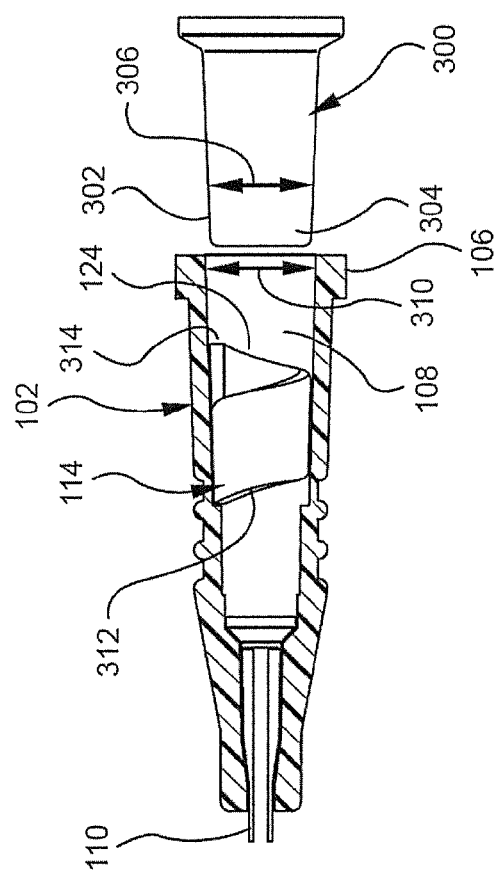
FIG. 3A is a perspective view of the blood control device of FIG. 1 after the needle has been withdrawn.

The illustrated embodiments of the present invention will be best understood by reference to the drawings, wherein like parts are designated by like numerals throughout. It will be readily understood that the components of the present invention, as generally described and illustrated in the Figures herein, may be arranged and designed in a wide variety of different configurations. Thus, the following more detailed description, as presented in the Figures, is not intended to limit the scope of the invention as claimed, but is merely representative of selected embodiments of the invention. The following description is intended only by way of example, and simply illustrates certain selected embodiments of devices, systems, and processes that are consistent with the invention as claimed herein.

As used in this specification, the term "needle" refers to any of various devices that may be used to pierce the skin to acquire intravenous access, such as a hypodermic needle, a hollow-bore needle, a surgical knife, and the like. The term "catheter adapter" refers to a medical device providing fluid communication and mechanical connection between an intravenous catheter and another vascular access device, such as a needle safety device, syringe, intravenous tubing, or the like. The term "Luer device" refers to a medical device that includes standard Luer taper dimensions, as set forth in the International Organization for Standardization ("ISO") 594 standards. These standardized taper dimensions enable one or more Luer devices to be interconnected by male and female interlocking features.

Referring now to FIG. 1, an intravenous catheter assembly 100 in accordance with the present invention may include a catheter adapter 102, a catheter 110, a needle 112, and a blood control valve 114. Each component 102, 110, 112, 114 of the intravenous catheter assembly 100 may align with the other along a longitudinal axis 122, and may be adapted for assembly as discussed in more detail below.

The catheter adapter 102 may be longitudinally oriented around the longitudinal axis 122 and may include a proximal end 104, a distal end 106, and a hollow interior region 108 extending therebetween. The proximal and distal ends 104, 106 may be configured to receive the needle 112 therethrough along the longitudinal axis 122. Specifically, the needle tip (not shown) may be introduced through the proximal end 104 of the catheter adapter 102 and extend through the hollow interior region 108 to exit the distal end 106 thereof. In some embodiments, the proximal and distal ends 104, 106 may include substantially smooth inner surfaces to facilitate manipulation of the needle 112 therethrough.

In one embodiment, an outer surface of the catheter adapter 102 may be substantially cylindrical and molded along the longitudinal axis 122 to provide a secure, comfortable grip. In some embodiments, for example, the catheter adapter 102 may include grooves, ridges or an otherwise textured outer surface to facilitate a secure grip.

The catheter adapter 102 may further include a catheter 110 extending from its distal end 106. The catheter 110 may be integral to the catheter adapter 102 or coupled thereto. The catheter adapter 102 and catheter 110 may cooperate to guide the needle 112 such that the needle tip (not shown) may protrude through the catheter 110 to facilitate an intravenous catheterization process. Likewise, the needle 112 may be selectively retracted from the catheter 110 and catheter adapter 102 after use.

A blood control valve 114 may be positioned within the hollow interior region 108 of the catheter adapter 102 to mediate fluid flow between the catheter 110 and the distal end 106 of the catheter adapter 102. The blood control valve 114 may include a substantially resilient helical outer shell 116 and an inner valve portion 118 formed therein. The outer shell 116 may include an elastomeric material such as silicone rubber, or any other suitable material known to those in the art. Likewise, the inner valve portion 118 may also be formed of an elastomeric or other suitable material.

The outer shell 116 may be oriented within the catheter adapter 102 such that an outer surface of the outer shell 116 lies substantially adjacent to an inner surface of the catheter adapter 102, with a distal edge 124 of the blood control valve 114 exposed within the hollow interior region 108.

The inner valve portion 118 formed within the outer shell 116 may include mating portions 120a, 120b. In some embodiments, the mating portions 120a, 120b may be substantially resilient and adapted to receive the needle 112 therebetween, thereby facilitating an intravenous catheterization procedure. Specifically, the needle tip (not shown) may be advanced through a mating junction 126 formed between the mating portions 120a, 120b, thereby deforming the mating portions 120a, 120b as needed to accommodate the diameter of the needle 112.

The mating portions 120a, 120b may otherwise substantially align where the outer shell 116 is in an uncompressed state. The mating junction 126 formed thereby may provide controlled fluid leakage to enable continued visibility of blood flashback throughout a catheter insertion procedure. This feature of the present invention may facilitate proper positioning of the catheter 110 within a blood vessel.

Referring now to FIG. 2, the needle 112 may be gradually retracted through the catheter 110 and catheter adapter 102 once the catheter 110 is properly positioned within a blood vessel. In some embodiments, the needle 112 and the blood control valve 114 may cooperate to enable continued visibility of blood flashback throughout such an intravenous catheterization procedure, thereby providing continuing confirmation that the catheter 110 is properly positioned within the blood vessel.

Particularly, a flashback chamber (not shown) attached to a distal end (not shown) of the needle 112 may enable a health care worker to visualize blood flashback within the flashback chamber upon piercing a blood vessel with the needle 112.

The angle at which the needle 112 and catheter 110 are set may then be lowered to facilitate advancement of the catheter 110 into the blood vessel. The needle 112 may be gradually retracted from within the catheter 110, thereby releasing a seal between the needle 112 and catheter 110 and creating an annular space 204 between the proximal end (not shown) of the catheter 110 and the needle tip 202. Blood flashback may gradually fill this annular space 204, providing continued evidence of proper positioning of the catheter 110 within the blood vessel.

Finally, the catheter 110 may be advanced within the blood vessel until the proximal end 104 of the catheter adapter 102 reaches the patient's skin. The needle 112 may then be withdrawn in a direction 200 such that the needle tip 202 exits the catheter 110, the blood control valve 114, and finally the distal end 106 of the catheter adapter 102. The resiliency of the mating portions 120a, 120b forming the inner valve portion 118 of the blood control valve 114 may cause the mating portions 120a, 120b to substantially re-align following retraction of the needle tip 202 beyond the mating junction 126. While this re-alignment effectively prevents a free flow of blood into the catheter adapter 102 upon withdrawal of the needle 112 and without requiring digital occlusion of the blood vessel, the blood control valve 114 continues to permit controlled, visible fluid leakage past the mating junction 126 and into a distal portion of the catheter adapter 102. This feature of the present invention may enable final confirmation that the catheter 110 is properly positioned within the blood vessel.

Figure 3B:
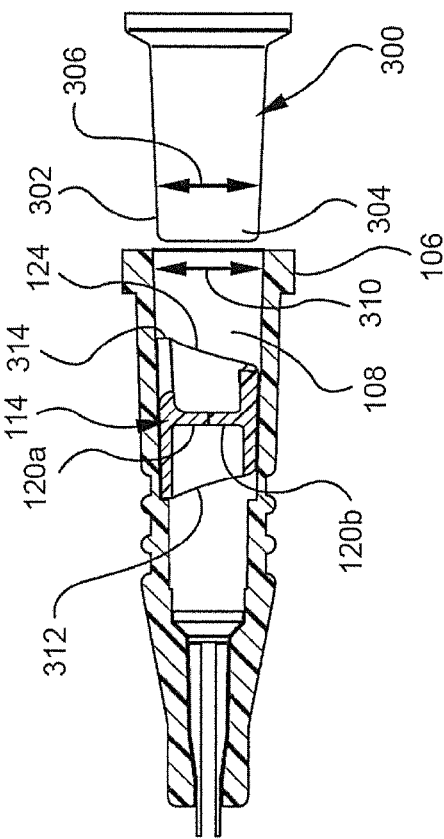
FIG. 3B is a cross-sectional view of the blood control device of FIG. 3A depicting relative positioning of the plates forming the inner valve portion.

Referring now to FIGS. 3A and 3B, a catheter adapter 102 housing a blood control valve 114 in accordance with the present invention may be configured to accommodate a Luer device 300 inserted into the distal end 106 thereof. A Luer device 300 may include, for example, a syringe, a catheter, a hubbed needle, an intravenous tube, a fluid administration set, or any other such device known to those in the art. The Luer device 300 may include a taper 302 having an outside diameter 306 at least slightly less than an inside diameter 310 of the distal end 106 of the catheter adapter 102. The dimensions of the taper 302 and the diameters 306, 310 of the taper 302 and distal end 106 of the catheter adapter 102 however, may vary within standard tolerances known to those in the art.

The blood control valve 114 may be positioned within the hollow interior region 108 of the catheter adapter 102 such that the blood control valve 114 may be effectively compressed by inserting the Luer device 300 into the distal end 106 of the catheter adapter 102. Specifically, in some embodiments, the helical shape of the outer shell 116 of the blood control valve 114 may result in the distal and proximal edges 124, 312 being angled with respect to one another, and being further angled with respect to the distal end 106 of the catheter adapter 102. In this position, the inner valve portion 118 of the blood control valve 114 may be substantially closed such that, in certain embodiments, the mating portions 120a, 120b are substantially aligned.

The proximal end 304 of the Luer device 300 may be substantially parallel to the distal end 106 of the catheter adapter 102. In this manner, insertion of the proximal end 304 of the Luer device 300 into the distal end 106 of the catheter adapter 102 may result in the outer shell 116 being progressively compressed from its most distal tip 314, as discussed in more detail below.

Figure 4A:
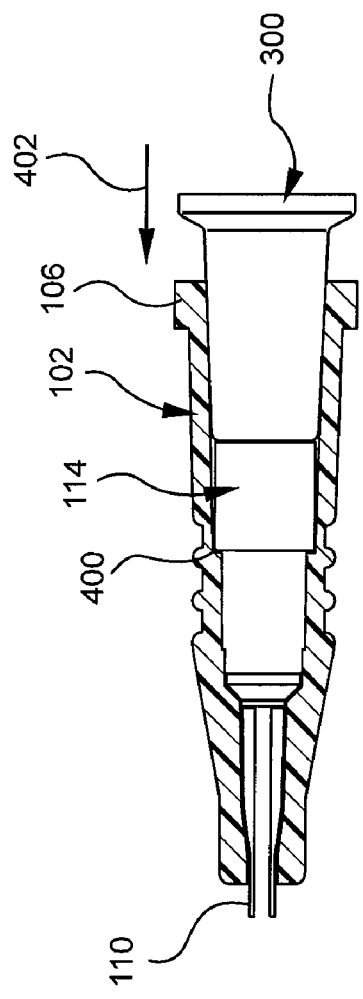
FIG. 4A is a perspective view of the blood control device of FIG. 1 upon insertion of a Luer device in accordance with certain embodiments of the present invention.
Figure 4B:
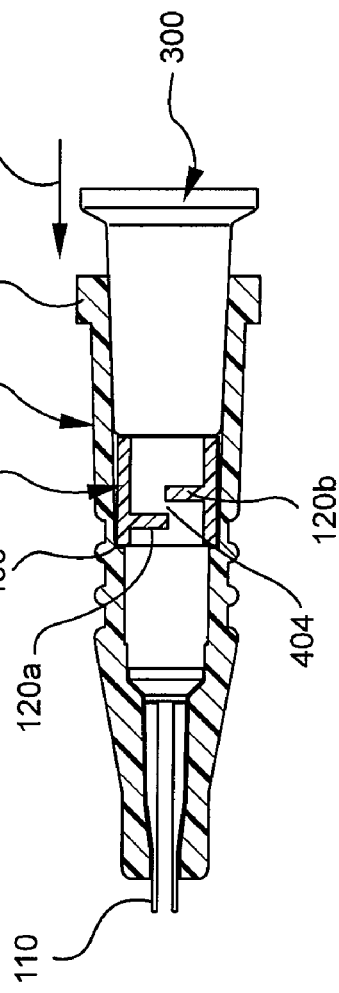
FIG. 4B is a cross-sectional view of the blood control device of FIG. 4A depicting relative positioning of the plates forming the inner valve portion.

Referring now to FIGS. 4A and 4B, inserting the Luer device 300 into the distal end 106 of the catheter adapter 102 may compress the blood control valve 114 residing therein. Specifically, the proximal end 304 of the Luer device 300 may initially contact the most distal tip 314 of the outer shell 116 and progressively urge the distal edge 124 towards the proximal end 104 of the catheter adapter 102.

In certain embodiments, the catheter adapter 102 may include a shoulder 400 to define a position within the hollow interior region 108 that is substantially perpendicular to the longitudinal axis 122, and limit translation of the blood control valve 114 beyond that position. In such embodiments, inserting the Luer device 300 into the catheter adapter 102 may urge the distal edge 124 of the outer shell 116 in a direction 402 towards the shoulder 400. Depending on the initial position of the blood control valve 114 within the hollow interior region 108, inserting the Luer device 300 further into the catheter adapter 102 may translate the blood control valve 114 within the hollow interior region 116 in the same direction 402. The shoulder 400, however, may limit translation of the blood control valve 114 in the direction 402 beyond a position where the proximal edge 312 of the outer shell 116 substantially contacts the shoulder 400.

Compression of the blood control valve 114 in this manner may skew the helical outer shell 116, thereby opening the inner valve portion 118 to create a fluid path 404. Particularly, as discussed in more detail below, mating portions 120a, 120b forming the inner valve portion 118 may misalign to permit controlled fluid flow from the Luer device 300 through the blood control valve 114, in a direction 402 towards the proximal end 104 of the catheter adapter 102 and attached catheter 110.

Figure 5:
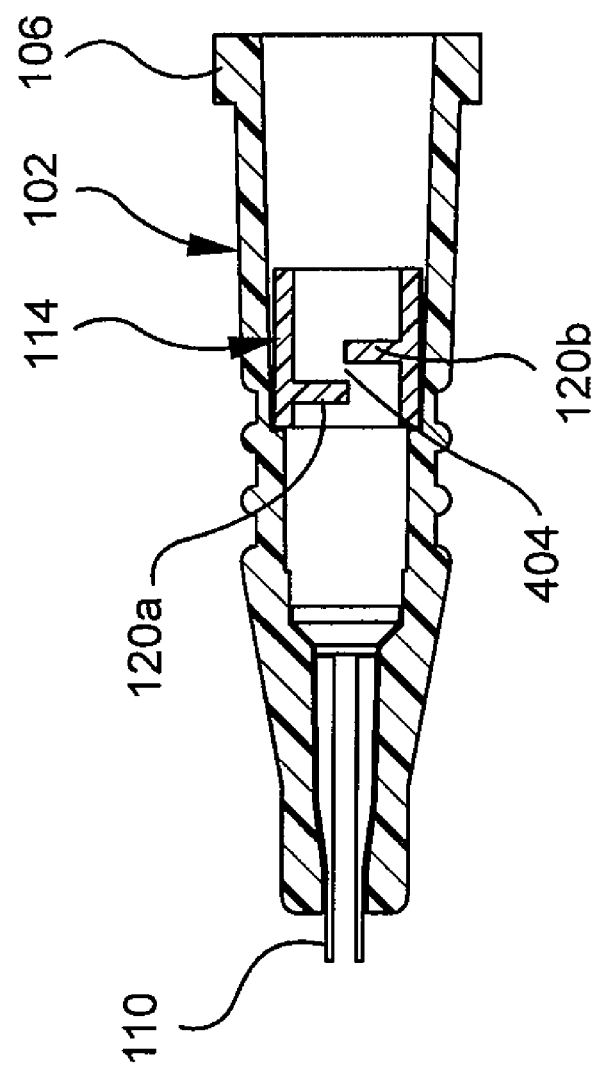
FIG. 5 is a cross-sectional view of one embodiment of a blood control device in accordance with the present invention after removal of a Luer device from the intravenous catheter assembly.

Withdrawing the Luer device 300 from the catheter adapter 102 may release the blood control valve 114 from its compressed position, enabling the mating portions 120a, 120b to realign to substantially close the inner valve portion 118. Alternatively, as shown in FIG. 5, the helical outer shell 116 may remain skewed following withdrawal of the Luer device 300 from the catheter adapter 102. In this case, the mating portions 120a, 120b may remain in a misaligned state, thereby maintaining a fluid path 404 between the Luer device 300 and proximal end 104 of the catheter adapter 102.

Figure 6:
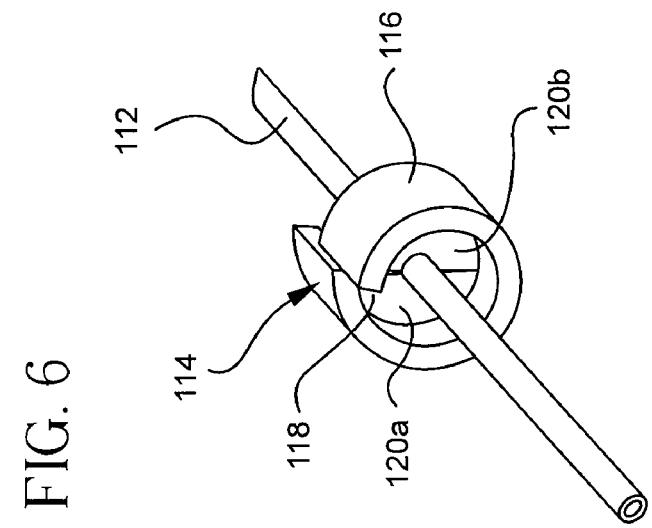
FIG. 6 is a perspective view of one embodiment of a blood control device having a needle inserted therein in accordance with the present invention.

Referring now to FIG. 6, like the outer shell 116, the inner valve portion 118 of the blood control valve 114 may be formed of a substantially elastomeric material such as silicone rubber, or other suitable material known to those in the art. As a result, the mating portions 120a, 120b that constitute the inner valve portion 118 may deform as needed to accommodate an introducer needle 112 inserted therethrough. This feature may enable simple manufacture and/or retrofitting of an intravenous catheter assembly incorporating a blood control valve 114 in accordance with the present invention, while optimizing blood control and flashback visibility throughout an intravenous catheterization procedure.

While deformation of the mating portions 120a, 120b to accommodate the needle 112 may enable slightly increased fluid leakage into the distal end 106 of the catheter adapter 102 while the needle 112 extends through the mating junction 126, the resilient nature of the mating portions 120a, 120b may continue to limit fluid leakage to provide an increased time during which to perform an intravenous catheterization procedure and minimize the amount of physical manipulation required for the same. In this manner, embodiments of the present invention may significantly reduce a possibility of blood flashback overfilling the catheter adapter 102 during an intravenous catheterization procedure and causing injuries related to blood exposure.

Figure 7A:
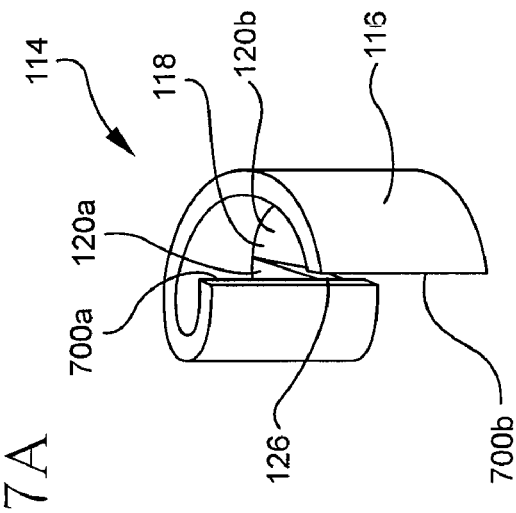
FIG. 7A is a perspective view of one embodiment of a blood control device following removal of a needle in accordance with certain embodiments of the present invention.
Figure 7B:
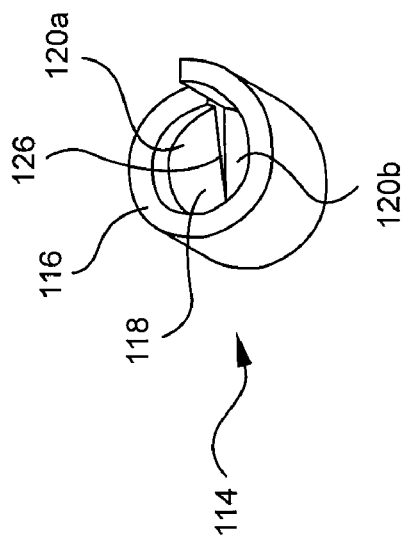
FIG. 7B is an alternative perspective view of the blood control device of FIG. 7A.

Referring now to FIGS. 7A and 7B, and as mentioned above, a blood control valve 114 in accordance with certain embodiments of the present invention may be substantially monolithic in nature, such that the inner valve portion 118 is an integral part of the outer shell 116. Alternatively, the outer shell 116 and inner valve portion 118 may be molded independently of each other and coupled together such that the inner valve portion 118 extends circumferentially inwardly from the outer shell 116 to substantially occupy an annular space formed by the helical outer shell 116 in its uncompressed state.

In any case, the substantially helical outer shell 116 may include lateral edges 700a, 700b that are skewed with respect to one another. As previously discussed, the inner valve portion 118 may include mating portions 120a, 120b that extend inwardly from the outer shell 116 to form a substantially linear mating junction 126 when the outer shell 116 is in its uncompressed state.

Figure 8:
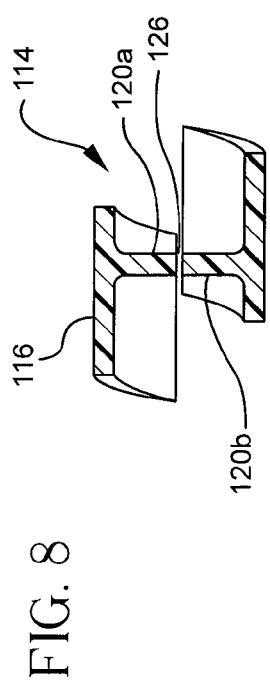
FIG. 8 is a cross-sectional view of the blood control device of FIG. 7A showing relative positioning of the plates forming the inner valve portion.

Referring now to FIG. 8, the mating junction 126 formed by the mating portions 120a, 120b of the inner valve portion 118 where the outer shell 116 is in its uncompressed state may substantially block fluid flow therethrough. Because the mating junction 126 is not a sealing junction, however, fluid may nevertheless slowly seep through the mating junction 126 to enable continued flashback visibility after the needle 112 has been removed. This continued controlled fluid leakage through the blood control valve 114 of the present invention facilitates accuracy and efficiency in performing intravenous catheterization procedures.

Figure 9A:
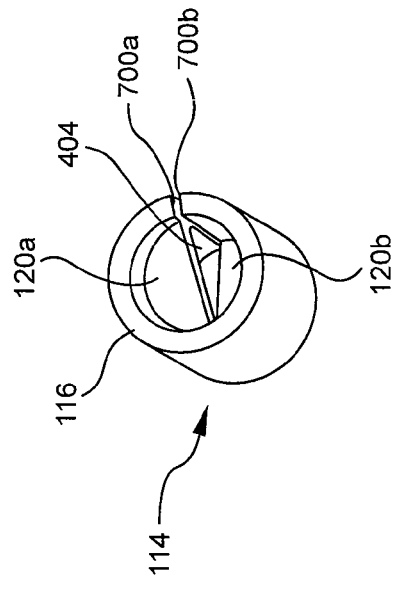
FIG. 9A is a perspective view of one embodiment of a blood control device actuated to provide a fluid flow path in accordance with the present invention.
Figure 9B:
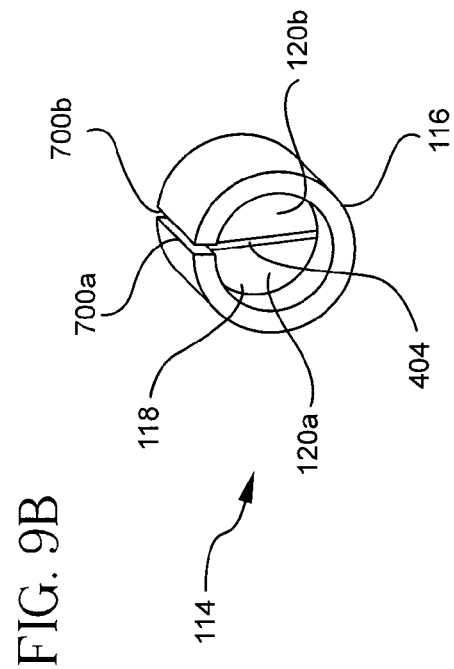
FIG. 9B is an alternative perspective view of the blood control device of FIG. 9A.
Figure 10:
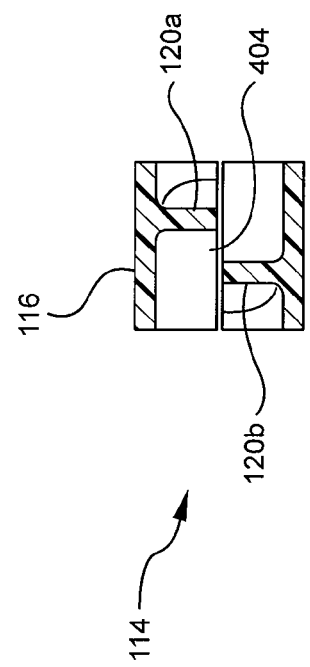
FIG. 10 is a cross-sectional view of the blood control device of FIG. 9A showing relative positioning of the plates forming the inner valve portion and the fluid path thereby created.

Referring now to FIGS. 9A, 9B, and 10, compressing the substantially resilient helical outer shell 116 may open the inner valve portion 118 at the mating junction 126, thereby creating a fluid path 404 between the mating portions 120a, 120b. Specifically, depending on the compressive force applied, the lateral edges 700a, 700b of the outer shell 116 may be brought into substantial alignment with each other. This distortion of the otherwise helical shape of the outer shell 116 may in turn misalign the mating portions 120a, 120b to create a fluid path 404.

A flow rate through the fluid path 404 may be varied by varying the compressive force applied to the outer shell 116, thereby enabling controlled fluid flow through the blood control valve 114. Specifically, an increase in applied compressive force may result in less restricted fluid flow and a faster flow rate through the blood control valve 114. In some embodiments, controlled variation in applied compressive force may be achieved by selecting a Luer device 300 having specific taper 302 dimensions, varying a force with which the Luer device 300 is inserted into the catheter adapter 102, varying positioning of the blood control valve 114 within the hollow interior region 108 of the catheter adapter 102, and/or by any other means known to those in the art.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A septum to control blood flow through an intravenous catheter, the septum comprising:
   an outer shell having an inner surface, an outer surface, a first lateral edge, and a second lateral edge, the outer shell being wrapped in a substantially helical shape, the outer shell being movable between an uncompressed state in which the first lateral edge is positionally skewed from the second lateral edge and a compressed state in which the second lateral edge and the first lateral edge are aligned; and an inner valve coupled to the inner surface, the inner valve being closed when the outer shell is in the uncompressed shape, the inner valve being open when the outer shell is in the compressed state.

2. The septum of claim 1, wherein the outer shell comprises an substantially resilient elastomeric material.

3. The septum of claim 2, wherein the elastomeric material comprises silicone rubber.

4. The septum of claim 1, wherein the inner valve further comprises a first mating portion and a second mating portion that substantially align when the outer shell is in the uncompressed state.

5. The septum of claim 4, wherein a surface of the first mating portion is misaligned with a surface of the second mating portion when the outer shell is in the compressed state.

6. The septum of claim 4, wherein the first and second mating portions are configured to accommodate passage of a needle therebetween.

7. The septum of claim 1, wherein the outer shell is configured to be retained within a catheter adapter.

8. The septum of claim 7, wherein a position of the septum within the catheter adapter permits access to the outer shell via a Luer device inserted into an opening of the catheter adapter, wherein the Luer device compresses the outer shell from the uncompressed state to the compressed state.

9. The septum of claim 8, wherein in the compressed state a portion of the outer shell translates within the catheter adapter towards a catheter coupled to an end of the catheter adapter.

10. A method to control blood flow through an intravenous catheter, the method comprising:
Providing an outer shell having an inner surface, an outer surface, a first lateral edge, and a second lateral edge, the outer shell being wrapped in a substantially helical shape, the outer shell being movable between an uncompressed state in which the first lateral edge is positionally skewed from the second lateral edge and a compressed state in which the second lateral edge and the first lateral edge are aligned;
coupling an inner valve to the inner surface of the outer shell, the inner valve being closed when the outer shell is in the uncompressed shape, the inner valve being open when the outer shell is in the compressed state; and
positioning the outer shell within a catheter adapter such that a portion of the outer shell is accessible to a Luer device inserted into the catheter adapter, wherein the Luer device compresses the outer shell to substantially align the first and second lateral edges thereby opening a fluid pathway through the inner valve.

11. The method of claim 10, wherein the inner valve comprises a first mating portion and a second mating portion that substantially align when the outer shell is in the uncompressed state.

12. The method of claim 11, wherein when the outer shell is in the compressed state, the first and second mating portions misalign to create a fluid path.

13. The method of claim 11, wherein the first and second mating portions comprise a substantially resilient elastomeric material.

14. The method of claim 13, wherein the first and second mating portions are configured to selectively deform to permit passage of a needle therebetween.

15. The method of claim 10, wherein the outer shell comprises an elastomeric material.

16. The method of claim 10, further comprising inserting the Luer device into an opening of the catheter adapter to contact and compress the outer shell.

17. The method of claim 16, wherein upon compressing the outer shell with the inserted Luer device, at least a portion of the outer shell translates within the catheter adapter towards a catheter coupled to an end of the catheter adapter.

18. A septum to control blood flow through an intravenous catheter, the septum comprising:
a outer shell having an inner surface and an outer surface, the outer shell being wrapped in a substantially helical shape, the outer shell being movable between an uncompressed state and a compressed state; and
an inner valve coupled to the inner surface, the inner valve having a first mating portion and a second mating portion that are substantially aligned when the outer shell is in the uncompressed state and that are misaligned when the outer shell is in the compressed state.

19. The septum of claim 18, wherein the outer shell further has a first lateral edge and a second lateral edge, in the uncompressed state the first lateral edge is positionally skewed from the second lateral edge and in the compressed state the second lateral edge and the first lateral edge are aligned.

20. The septum of claim 18, wherein the outer shell is configured to be retained within a catheter adapter.

* * * * *